United States Patent [19]

Cholcha

[11] Patent Number: 5,186,925
[45] Date of Patent: Feb. 16, 1993

[54] NITROGLYCERIN PUMP SPRAY

[75] Inventor: Walter Cholcha, Elmshorn, Fed. Rep. of Germany

[73] Assignee: G. Pohl-Boskamp GmbH & Co., Hohenlockstedt, Fed. Rep. of Germany

[21] Appl. No.: 665,087

[22] Filed: Mar. 6, 1991

[30] Foreign Application Priority Data

Mar. 10, 1990 [DE] Fed. Rep. of Germany ....... 4007705

[51] Int. Cl.$^5$ .......................... A61K 9/08; A61K 9/12
[52] U.S. Cl. ........................................ 424/43; 424/45; 424/47; 424/456; 514/509; 514/824; 558/486
[58] Field of Search .................... 424/47, 456, 45, 43; 514/824, 509; 558/486

[56] References Cited

U.S. PATENT DOCUMENTS

| | | | |
|---|---|---|---|
| 4,336,243 | 6/1982 | Sanvordeker et al. | 424/449 |
| 4,885,173 | 12/1989 | Stanley et al. | 424/440 |
| 4,919,919 | 4/1990 | Aouda et al. | 424/45 |
| 4,976,965 | 12/1990 | Block et al. | 424/456 |
| 5,047,230 | 9/1991 | Nagy et al. | 424/45 |

OTHER PUBLICATIONS

"Stuart's Isosorbide Acute Angina Indication Should be Changed", Scrip No. 372 (Mar. 1979), p. 18.

Martindale: The Extra Pharmacopoeia, 29th ed., (Ed. by James E. F. Reynolds); publ. by The Pharmaceutical Press, London, (1989), p. 1428.

Primary Examiner—Thurman K. Page
Assistant Examiner—Robert H. Harrison
Attorney, Agent, or Firm—Cushman, Darby & Cushman

[57] ABSTRACT

The invention relates to a nitroglycerin pump spray containing 0.2 to 3.5% by wt. of nitroglycerin and up to 3% by wt. of customary additives such as flavoring agent or antioxidants and a liquid phase consisting of aliphatic $C_2$ to $C_4$ alcohols and a vehicle and is characterized in that the liquid phase consists of 10 to 40% by wt. of ethyl alcohol and 90 to 60% by wt. of a neutral oil.

5 Claims, No Drawings

NITROGLYCERIN PUMP SPRAY

FIELD OF THE INVENTION

The invention relates to a nitroglycerin pump spray containing 0.2 to 3.5% by wt. of nitroglycerin and up to 3% by wt. of customary additives such as flavouring agent or antioxidants.

BACKGROUND OF THE INVENTION

Nitroglycerin preparations or glyceryl trinitrate are used preferably sublingually for the arrest and prophylaxis of angina pectoris attacks, in the case of myocardial infarction, pulmonary oedema, asthma cardiale, coronary sclerosis, spastic migraine and spastic bile duct colic, and lead to a prompt effect on the pain or critical heart-circulatory conditions with a reduced blood flow and increased pressure in the ventricles.

In the case of sprayable aerosol sprays to be applied sublingually, preparations have been used hitherto which contain, in addition to nitroglycerin and customary additives, a neutral oil as vehicle and 70 to 95% by wt. of propellant such as dichlorotetrafluoromethane and are described, for example, in DE-PS 32 46 081. Although these nitroglycerin-containing aerosol preparations guarantee a therapeutically effective blood level within a short period, they have the disadvantage that they can be harmful to the environment because of the fluorochlorohydrocarbon propellants present.

Consequently, propellant-free aerosol preparations were proposed, namely so-called pump sprays e.g. according to DE-OS 39 22 650, in which the liquid phase is composed of aliphatic $C_2$ to $C_4$ alcohols and a vehicle. In these nitroglycerin pump sprays, the $C_2$ to $C_4$ alcohol content is said to be 51 to 90% by wt. and, moreover, a polyalkylene glycol or a $C_2$ to $C_8$ alcohol having several hydroxy groups is said to be provided as vehicle.

Preparations of this kind have the disadvantage that, in view of the high alcohol content, approximately 30% of the output quantity of approximately 50 mg present in the metering chamber of the pump spray device evaporates after only a short storage period, with the result that the first squirt contains only 35 mg of the active substance solution instead of the clinically required quantity of approximately 50 mg. This loss of active substance solution is too great for a drug which is used for the immediate treatment of acute angina pectoris attacks and its use can not, therefore, be justified from a therapeutic aspect. Moreover, a blockage of the valves can also be brought about as a result of the evaporation of ethyl alcohol, which completely precludes the application of a metered dose. In the case of lingual application, the high $C_2$ to $C_4$ alcohol and preferably ethyl alcohol content also has the disadvantage that the mucosa in the lingual region is excessively stimulated and the plasma level rises too high very rapidly in comparison with equivalent preparations which have been proven in therapeutic use for decades. This can lead to vasomotor headaches, orthostatic dysregulation, a feeling of weakness or a dazed state. Moreover, drugs with high concentrations of alcohol are unsuitable for certain groups of patients (e.g. pregnant women, persons with alcohol dependency, persons with liver or kidney damage) and give rise to considerable safety problems in production and storage.

Apart from the excessively high ethyl alcohol content of this propellant-free aerosol preparation, a polyalkylene glycol or a $C_2$ to $C_8$ polyhydroxy alcohol is proposed as vehicle which are usually irritating to the mucosa or toxicologically harmful.

OBJECTS OF THE INVENTION

Therefore, it is an object of the invention to provide a nitroglycerin pump spray whose liquid phase is of a nature such that, in the required immediate effective treatment of acute life-threatening conditions, the first squirt immediately releases the requisite quantity of active substance even after storage.

It is a further object of the invention to provide a nitroglycerin pump spray whose liquid phase is of a nature such that, with the first squirt the therapeutically sufficient plasma levels in respect of nitroglycerin are not substantially exceeded.

It is also an object of the invention to provide a nitroglycerin pump spray which contains less alcohol so that it is better suited for the above mentioned groups of patients and is safer to handle in production and storage.

It is an additional object of the invention to provide a nitroglycerin pump spray in which the liquid phase comprises a vehicle which is neither irritating to the mucosa nor toxicologically harmful.

SUMMARY OF THE INVENTION

The invention is directed to a nitroglycerin pump spray containing 0.2 to 3.5% by wt. of nitroglycerin and up to 3% by wt. of customary additives such as flavoring agent or antioxidants and a liquid phase consisting of aliphatic $C_2$ to $C_4$ alcohols and a vehicle, which is characterized in that the liquid phase consists of 10 to 40% by wt. of ethyl alcohol and 90 to 60% by wt. of a neutral oil.

Preferred embodiments and advantages of the invention will become apparent from the following detailed description of the invention and the sub-claims.

DETAILED DESCRIPTION OF THE INVENTION

Surprisingly, it has become apparent that a pump spray with the liquid phase consisting of 10 to 40% by wt. of ethyl alcohol and 90 to 60% by wt. of a neutral oil still produces a uniform mist and a sufficient quantity of the preparation or active substance is still available after a relatively long storage time. Even if, after 7 days' storage, a quantity loss of max. 10%, based on the active substance solution present in the metering chamber, is recorded in the first squirt, the loss of active substance is smaller because the latter remains dissolved in the less readily evaporable neutral oil.

In the case of the nitroglycerin pump spray according to the invention, the nitroglycerin is provided in an approximately 5% oily solution and then mixed with the other requisite quantities of neutral oil and optionally with other additives and transferred to the pump spray bottles with the addition of ethyl alcohol.

All fatty oils can be used as neutral oils. Synthetic triglycerides whose fatty acid proportion is composed of saturated $C_8$ to $C_{12}$ fatty acids are, however, preferred. These triglycerides are also known as Miglyol types. Various types of Miglyol are distinguished according to the caprylic acid ($C_{8:0}$) and capric acid ($C_{10:0}$) content.

| For example, Miglyol 812 contains | |
|---|---|
| caprylic acid: | 50–65% |
| capric acid: | 30–45% |

| -continued | |
|---|---|
| whilst Miglyol 810 contains | |
| caprylic acid: | 65–75% |
| capric acid: | 25–35%. |

Natural oils can also be used however, in which case those oils that contain as few unsaturated fatty acids as possible are preferred. This can be achieved by hydrogenation in the case of oils which contain a large quantity of unsaturated fatty acids. The proportion of the neutral oil in the nitroglycerin pump spray according to the invention is 90 to 60% by wt. but is usually 85 to 70% by weight; neutral oil quantities of about 80% by wt. are preferred.

The nitroglycerin proportion in the spray according to the invention can vary but is usually between 0.1 and 2% by weight. Nitroglycerin contents of 0.6 to 0.9% by wt., for example 0.8% by wt., are preferred.

In addition to the above-mentioned principal constituents, the nitroglycerin pump spray according to the invention can contain customary additives such as flavouring agents, for example peppermint oil or menthol, which give the spray a refreshing taste. The flavouring agents are mostly present in a quantity of approximately 0.1 to 1% by wt. and preferably 0.4 to 0.8% by weight. When the spray is used, the output quantities are approximately 25 to 100 mg and preferably 50 mg per squirt.

The invention will be explained in more detail below on the basis of examples.

EXAMPLE 1

A nitroglycerin pump spray with the following composition was prepared:

| nitroglycerin, 5% in Miglyol 812 (TM) | 20.1% by wt. |
|---|---|
| ethanol | 20.0% by wt. |
| Miglyol 812 (TM) | 59.2% by wt. |

| -continued | |
|---|---|
| spearmint oil | 0.7% by wt. |

After 7 days' storage at room temperature, the percentage deviation in the output quantity of the first squirt from the required value was 10%.

In the case of a comparative preparation according to Example 1 of DE-OS 39 22 650, the deviation in the output quantity of the first squirt from the required value was 33%. This is too large for a drug for treating attacks in which the very first squirt must provide a sufficient quantity of active substance solution.

EXAMPLE 2

A nitroglycerin pump spray similar to that of Example 1 was prepared in which, however, instead of 59.2% by wt. of Miglyol 812 the same quantity of rape oil and in a further preparation the same quantity of Miglyol 810 were now used. In both cases, the preparation behaved in the same way as that of Example 1; a uniform mist was formed. After 7 days' storage, the output quantity of the first squirt was somewhat more than 90%, based on the required value.

I claim:

1. Nitroglycerin pump spray containing 0.2 to 3.5% by wt. of nitroglycerin and up to 3% by wt. of additives selected from the group consisting of flavouring agents and antioxidants, and a liquid phase consisting of 10 to 40% by wt. of ethyl alcohol and 90 to 60% by wt. of synthetic or natural fatty oils.

2. Nitroglycerin pump spray according to claim 1, wherein the liquid phase consists of 15 to 30% by wt. of ethyl alcohol and 85 to 70% by wt. of said fatty oils.

3. Nitroglycerin pump spray according to claim 1, wherein the liquid phase consists of about 20% by wt. of ethyl alcohol and about 80% by wt. of said fatty oils.

4. Nitroglycerin pump spray according to claim 1, wherein said fatty oils are selected from the group consisting of a saturated natural oil and a $C_8$ to $C_{12}$ fatty acid triglyceride.

5. Nitroglycerin pump spray according to claim 4, wherein said saturated natural oil is rape oil.

* * * * *